United States Patent [19]

McGowan et al.

[11] 4,363,968

[45] Dec. 14, 1982

[54] METHOD AND APPARATUS FOR DETERMINING THE BINDER CONTENT IN A FIBROUS MAT

[75] Inventors: Paul T. McGowan, Granville; Raymond E. Wright, Newark, both of Ohio

[73] Assignee: Owens-Corning Fiberglas Corporation, Toledo, Ohio

[21] Appl. No.: 290,650

[22] Filed: Aug. 7, 1981

Related U.S. Application Data

[63] Continuation of Ser. No. 58,636, Jul. 19, 1979, abandoned.

[51] Int. Cl.$^3$ .............................................. G01J 1/00
[52] U.S. Cl. .................................... 250/339; 250/341
[58] Field of Search ............... 250/338, 339, 340, 341, 250/358.1, 359.1, 360.1; 356/429, 432, 237, 238; 65/14, 264.12; 156/379, 379.6, 380.9

[56] References Cited

U.S. PATENT DOCUMENTS

| | | | |
|---|---|---|---|
| 3,405,268 | 10/1968 | Brunton | 250/339 |
| 3,560,179 | 2/1971 | Kleist | 65/14 |
| 3,851,175 | 11/1974 | Dahlin et al. | 250/339 |
| 3,877,818 | 4/1975 | Button et al. | 250/339 |
| 4,006,358 | 2/1977 | Howarth | 250/339 |
| 4,097,743 | 6/1978 | Carlson | 250/339 |

Primary Examiner—Alfred E. Smith
Assistant Examiner—Janice A. Howell
Attorney, Agent, or Firm—Ronald C. Hudgens; Patrick P. Pacella; Ted C. Gillespie

[57] ABSTRACT

A method and apparatus are disclosed for measuring the amount of binder or of a particular constituent of that binder dispersed within a fibrous mat. The binder may typically be a suspension of one or more solids in a liquid carrier such as water. A radiation source is provided at a first wave length which is highly responsive to the presence of the binder constituent dispersed within the mat. A second radiation source is provided at a second wave length which is substantially insensitive to the presence of the binder constituent within the mat. A ratio is taken of the transmitted energy at these two wave lengths through the mat and this ratio is used as an indication of the amount of the binder constituent. A third source of radiation and a third wave length is transmitted through the mat to provide an indication of the thickness or density of the mat, the third wave length being substantially unaffected by the presence of the binder constituent in the mat. This measured density is factored with the measured values of the binder taken from the transmitted energy levels at the first and second wave lengths to correct these measurements for the effect of the mat. As an alternative, the first and second wave lengths can be chosen to measure change in state of a binder constituent, such as a suspended solid, during cure.

7 Claims, 2 Drawing Figures

METHOD AND APPARATUS FOR DETERMINING THE BINDER CONTENT IN A FIBROUS MAT

This is a continuation of application Ser. No. 58,636, filed July 19, 1979, now abandoned.

BACKGROUND OF THE INVENTION

This invention relates to a device for measuring the amount of a first material dispersed within a second material and more particularly to the measurement of a binder dispersed in a mat of fibrous material such as a mat of glass fibers. The invention may be used to measure the moisture content in the binder or it may be used to measure any other constituent of the binder such as a solid material suspended in a liquid. It also may be used to measure a change in the amount of a constituent in the binder to determine the cure state.

Instruments for measuring moisture content, for example moisture within a fibrous body, are well known in the art. For example, U.S. Pat. No. 3,851,175 shows a moisture gauge for measuring the moisture content of a moving sheet of paper. Specifically, it uses radiated energies at two closely related wave lengths, a first wave length $L_1$ and a second wave length $L_2$. $L_1$ is a reference and is relatively insensitive to the moisture within the paper. $L_2$ is sensitive to the presence of moisture and is absorbed by the moisture within the paper. The energies at these two wave lengths are measured, after transmission through the paper, and an energy ratio is taken and converted to moisture by a calibration procedure. In actual use, a calibration curve is drawn wherein samples of predetermined moisture content are radiated and a ratio is taken. These ratios are plotted against the actual moisture content for use as a calibration curve.

Other devices known in the prior art add improvements to this basic idea. For example, U.S. Pat. No. 4,097,743 teaches the use of a set of two closely related wave length radiated energies to derive a ratio of transmitted energy through a material and further teaches the use of a second set of the two closely related energies directly transmitted without passing through the material for a control in determining the effect of temperature induced optical transmission changes and to cancel any variable as transmission changes from the moisture measurement.

Another U.S. Pat. No. 4,006,358 uses the same measurement technique and adds a filter which compensates for a change in optical transmission due to dirt collected on the instrument.

Still another U.S. Pat. No. 3,405,268 uses three sources at closely related wave lengths, a first wave length responsive to the moisture in a paper web, a second wave length not responsive to the moisture or the cellulose in the paper, and a third wave length that is responsive only to paper. The transmitted energy through the material at each of these wave lengths is detected and a first ratio of the energies at the first and second wave lengths is taken to determine the moisture in the web. A second ratio of the energy transmitted through the material at the third wave length to the energy at the second wave length is taken to determine the proportional cellulose content of the paper and the basis weight. These two ratios are then taken together to indicate the moisture content and the basis weight.

Of particular interest is U.S. Pat. No. 3,851,175 which shows the use of an opacity signal factored in with the ratio signal indicative of the transmitted energies at the two closely related wave lengths to indicate moisture. As described in that patent, the use of a ratio at the two closely related wave lengths does not provide a true indication of moisture content in paper where the content of the paper may vary especially due to different types of wood and wood mixtures used in making the paper. As described in that patent, it is necessary to use an opacity signal to determine the opacity or the degree to which energy at the energies may be transmitted through the paper. This opacity signal then is used in recognition of the special problem in measuring moisture content in paper. One problem presented by paper is the opacity changes due to the different mixture of woods in the paper. As explained, the variations in opacity of paper is due to the variations in the pulp fiber mix and produces variations in the signals indicative of the transmitted energy through the paper, ranging up to two orders of magnitudes. Therefore, the opacity signal is derived as the amplifier gain needed to maintain at a constant voltage the reference channels of the two related wave length energies so that their relationship is accurately determined and the ratio of the signals does not vary except due to moisture. Automatic gain control is in response to the variations in the opacity of the paper to maintain the amplification of the two channels for the two radiated energies so that the two signals and their ratio is indicative of the moisture content. Additionally, the opacity signal is used to correct the linear slope of the prederived plot of moisture versus the signal level ratio. It is used to adjust the ratio amplitude indicative of the moisture relative to different hardwood-softwood proportions with identical basis weights.

The prior art then shows the technique of using radiated energy at two closely related wave lengths, measuring the signal levels of energy transmitted through a sample at the two wave lengths and taking the ratio therebetween to establish moisture content. Further shown, particularly for use with determining moisture content in paper, are techniques for correcting the ratio measurement for the opacity of paper due to the variations in the softwood-hardwood pulp mixture as well as for dirt accumulated on the instrument which changes the effective intensity of the radiation.

However, the teachings of the prior art are limited to the special problem presented by changes in opacity of the sample and the effect of those changes on the measurement of moisture. The prior art techniques also are limited to measurement of moisture in wood pulp. The prior art measures the transmitted radiation through the moisture contained by the pulp or web. The radiation is attenuated by the moisture and the web. The ratio amplitude is altered to bring it into correspondence with a precalibrated curve for moisture within a sample web or pulp moisture of the same pulp consistency.

The prior art does not deal with nor teach the measurement of materials other than moisture within a fibrous body or change in amount of the materials as an indication of process state or material state, nor does it teach the solution of the problem presented by changes in weight upon the primary measurement or the manner in which the ambiguity introduced by the weight of the material into the primary measurement may be analyzed and the measurement corrected.

SUMMARY OF THE INVENTION

This invention is directed to measuring a property, which may be the amount of a first material or the amount of the first material as related to a process or material state condition of that first material, dispersed within a second material and particularly adjusting the measurement for the effect of the second material on the measured value of the first material so that the measurement of the first material is not distorted or rendered ambiguous by the influence of the second material.

To this end, the material may be radiated with a single energy source or energies at two closely related frequencies in accordance with known techniques and a ratio of transmitted energies through the material is derived. The energies at the two related wave lengths are chosen consistent with accepted practice. However, the practice of this invention does not require that this technique be utilized and where suitable, a single source of energy at a single frequency may be used to measure the amount of the first material. Further, any other suitable technique which provides a measurement of the first material dispersed within the second material may be used where the effect of the materials on the measurement may be analyzed and corrected according to the principles of the invention.

The radiated energies at the first and second wave lengths are chosen so that the first wave length $L1$ is responsive to the presence of the first material while the second wave length $L2$ is non-responsive to the presence of first material. Under these conditions, the amount of energy transmitted through the material at the first wave length $L1$ will change corresponding to and proportionally to the amount of the dispersed material. The second non-responsive wave length $L2$ provides a reference and removes all other random effects from the measurement. Where a single energy source is used, it may be desirable to average the measured value over a number of samples to eliminate similar extraneous effects from the measurement.

The presence of the second material, through which the first material is dispersed, has an effect on the amount of energy transmitted through the materials. Further, the first material will demonstrate a different transmission characteristic for the first and second said wave lengths, $L1$ and $L2$. The transmission characteristic through the first material varies as a function of a wave length and is different for the energy at the first wave length and for the energy at the second wave length even though the material does not vary. In addition to measuring the amount of first material dispersed within the second material the invention also contemplates using a separate source to measure the second material containing the first material and analyzing the measurements to derive or produce a corrected indication of the first material.

The material also is radiated with energy at a third wave length, $L3$, which substantially is non-responsive to the presence of the first material dispersed through the second material and provides an indication of the presence of the second material containing the first material, although not necessarily an exact indication. This measurement is related to the weight of the second material, and is then factored into the measurement of the first material to provide a correct indication of the first material.

The method of the invention may be thought of as a sequence where the material is radiated at the first and second wave length $L1$ and $L2$ and the ratio taken, and then immediately subsequent or simultaneously the material is radiated at the third wave length $L3$ to measure the weight for a given area of the material. This weight may be easily converted to density when material thickness is known. These two measurements are then analyzed through an algorithm to produce an adjusted and correct indication of the material dispersed through the second material or of the second material.

The invention is particularly useful in measuring the amount of binder dispersed through a fibrous mat such as glass fibrous insulation. The technique may be made selective of the binder constituent by selecting one of the two closely related wave lengths $L1$ and $L2$ to be sensitive to the presence of that constituent. It may be used to measure the degree of cure by choosing one of the two closely related wave lengths to be responsive to a change in the presence of a first material whose measured indication is related to cure. For example, the energy chosen having a first wave length would be responsive to water if it was desired to measure the moisture content of the binder carrier dispersed throughout the mat. Alternately, the first wave length could be chosen responsive to any one of the solid suspended particles within the binder such as phenolic resin where it was desired to measure that constituent of the binder. Where a change in the amount of water or phenolic resin or any other constituent could be related to a process or material state, the measurement would provide an indication of that process state. It should be recognized that this technique could be adapted to measuring other dispersed materials and should not be thought of as limited to measuring the dispersion of a liquid suspension within a fibrous body.

This invention should not be thought of as limited to the prior art technique of radiating at two closely related frequencies. The invention can also be used with any other technique which provides an indication of a first material dispersed through the second material.

BEST MODE OF CARRYING OUT THE INVENTION

A method and apparatus for producing discontinuous fibers and then directing those fibers into a mat-like structure of comparatively high density as shown in U.S. Pat. No. 3,560,179, the disclosure of which is incorporated herein. Within that patent is also shown apparatus for delivering a binder in the form of a solid suspension in a liquid which is generally sprayed on the fibers prior to collection of the fibers into the high density mass. While this patent describes a method of producing glass fibers, in particular a high density fibrous mat, it should be understood that this method and apparatus can be used with regard to any other application wherein a first material is dispersed in a second material such as a fibrous mat and for the purpose of determining the amount of the first material dispersed within said second material or for the purpose of using that measured amount as indication of a process or material state.

Figure 1:
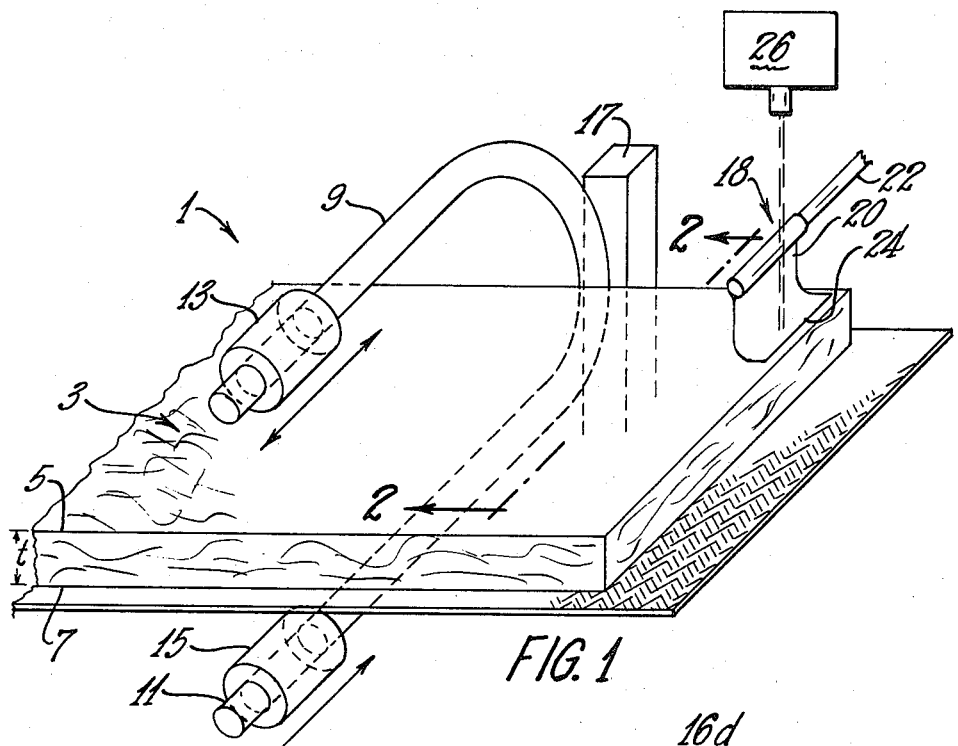
FIG. 1 is a fragmentary perspective view showing mounting the devide according to the principles of this invention over a fibrous mat production line and is in a schematic form.
Figure 2:
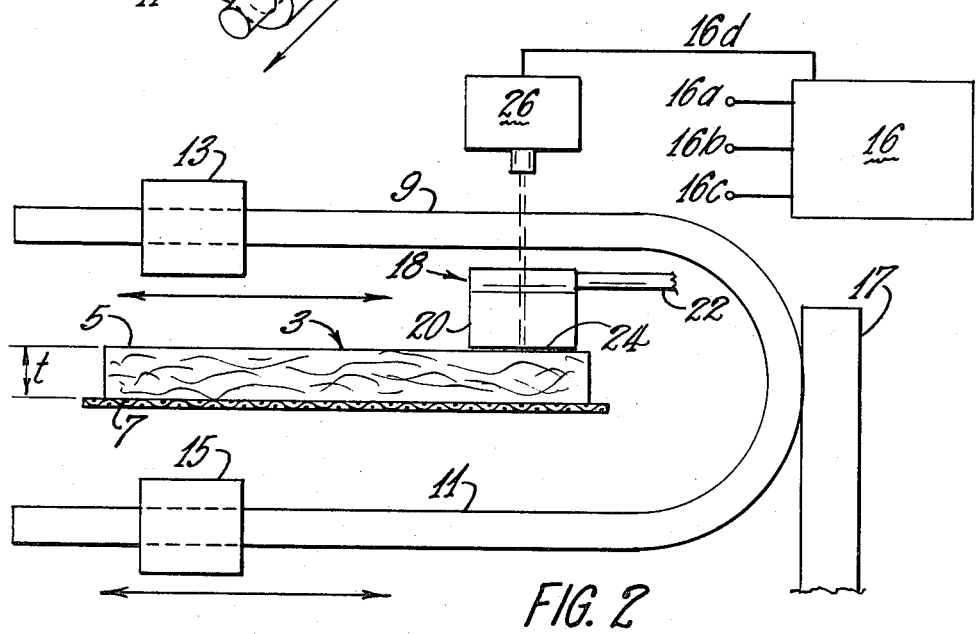
FIG. 2 is a cross-sectional view showing the same production line mounting as taken along line 2—2 in FIG. 1.

FIGS. 1 and 2 show a portion of a conveyor 1 carrying a high density mat 3. Suspended above the mat 3 over an upper mat surface 5 and under a lower mat surface 7 are a pair of parallel beams 9 and 11. Each beam 9 and 11 supports a traveling member shown as 13 for beam 9 and 15 for beam 11. The traveling members 13 and 15 are arranged directly opposite each other and are separated by the fibrous mat 3, the air gaps between the surface 5 of the mat and the member 13 and between surface 7 of the mat and the member 15. The two traveling members 13 and 15 are arranged to travel in unison so that the traveling member 15 is in vertical alignment with the traveling member 13 at all times. The exact nature of the frame 17 and beams 9 and 11 used to support the transmitter 13 and the detector 15 is not critical to the employment of the invention or to the principles of the invention.

The traveling members 13 and 15 contain the respective transmitters and receivers for the energy sources at frequencies chosen. Unit 13 may contain an infrared source capable of producing a signal of suitable intensity at wave lengths $L_1$ and $L_2$ and an x-ray or gamma-ray source of suitable intensity at wave length $L_3$. Unit 15 may contain such infrared detectors as an indium arsenide photo diode and an x-ray detector such as an ionization chamber. Any suitable mechanical arrangement may be utilized which maintains the relative alignment of the transmitter 13 with the receiver 15 as they travel on the beams 9 and 11. For example, as shown here, the units 13 and 15 may travel on beams 9 and 11 with the beams stationary or the transmitter 13 and the receiver 15 may be permanently mounted on the beams 9 and 11, respectively, and the post 17 may travel transverse to the direction of the movement of the mat 3.

A control unit 16 is provided for connection to the traversing transmitter unit 13 and receiver unit 15. Busses 16a and 16b may provide control signals to the traversing units 13 and 15 to direct their scanning movement and to return position signals to unit 16. A bus 16c provides the control unit 16 with the detected signals of radiant energy after passing through the material having thickness t. The control unit 16, such as a general purpose computer, may be any suitable known device capable of controlling the scanning process and then analyzing the resultant measuring signals.

A detector unit 18 provided is for measuring thickness t. This unit may be any suitable device such as a mechanical sensor or an ultrasonic sensor or a light sensor. An electro-mechanical sensor unit 18 is illustrated mounted on a support 22 and mounting a foil coated membrane 20 with the lower area 24 resting on the upper surface 5 of the mat 3. The membrane 20 is free to move under the force of the mat sliding underneath it. A pulsed sonic or microwave signal from transmitter 26 is directed at the portion 24 of the membrane 20 in contact with the mat to obtain a reflected wave which indicates the displacement of the membrane and the thickness of the mat. A cable 16d connects the detector 26 with the control unit 16 and to provide the control unit 16 with a signal indicative of the mat thickness t. The control unit 16 processes the signals indicative of radiating and transmitted radiant energy (Ioi and Ii) for each frequency $F_i$ and the signal indicative of the thickness t, according to the method of analysis decribed below.

A mechanical mat thickness sensor also may be used and can include a feeler gauge attached to a transducer and having one end resting on the mat. Increases in mat size would displace the feeler gauge. Gravity or other means urges the feeler gauge against the mat when it decreases in size. The transducer would provide a suitable electrical mat thickness signal to the control unit 16 in response to the feeler gauge movements.

Direct measurement of the amount of material, such as the binder, applied to the fibers provides an indication of the binder usage and permits a more exacting control of the binder usage and a greater control over the quality and cost of finished fibrous mat 3. Additionally, measurement of a first material amount initially suspended in the binder indicates the state of the process and is useful in the production of the mat for controlling the mat's characteristics and that of the binder.

In the course of measuring the first material, such as the binder applied to the fibers forming the mat, a source of radiation is employed which is responsive to the liquid part of the binder suspension. Additionally, radiation can be used which is responsive to the amount of solid material suspended in the binder liquid. The first material quantity may be constant over the process cycle and the measured property of the first material can be used as an indication of the amount of the first material dispersed in the second material or as an indication of the amount of the first material contained in a solution or suspension applied to the second material. Where the first material quantity changes over the process cycle then the measured property may be used as an indication of a point reached in the process cycle or material cycle.

In the course of measuring either the liquid vehicle or the suspended solids, the fibrous mat will affect the radiation transmissibility characteristic used to measure the liquid vehicle or the solids. For example, when it is desired to measure the amount of liquid, radiation having a frequency most responsive to that liquid is employed. The attenuation of the radiation is affected by the amount of vehicle applied to the fibers. However, the tranmissibility characteristic also is affected by the weight of the fiber. While the weight of the fiber is held within a close tolerance, the weight does vary and these variations will have an affect upon the attenuation and transmissibility of the radiation used for detecting the vehicle and the solids.

A standard measurement technique, as explained above, is to use two closely related frequencies within a common band of frequencies. One of the chosen frequencies $(f=1)$ is responsive to the measured constituent, either the liquid carrier or the solid material suspended in the carrier, and the other frequency $(f=2)$ is a reference and substantially non-responsive to the liquid or the suspended solid material. These two frequencies are then radiated by the transmitter 13 through the materials. The ratio of energy at $f=1$ transmitted through the materials to the energy transmitted through the materials at $f=2$ will provide an indication of the amount of the first material in the mass. This concept is shown in the prior art and is disclosed in U.S. Pat. No. 4,006,358.

However, one of the problems with this measurement technique is that the second material, in this case the fiber mat, affects the transmission of the energies at $f=1$ and $f=2$. Viewing the total measurement, the transmissibility of the energies at $f=1$ and $f=2$ are affected by both the first material and the second material. A change in the ratio of the energy transmitted through the materials at frequencies f=1 and f=2 is indeterminate, it not being known whether the change is due to the amount of the first material in the second material or due to a change in the second material.

As stated previously an object of this invention is to produce an indication of the amount of a first material dispersed through a second material and of the second material where the presence of the second material affects the measurement of the dispersed first material. The particular utility shown is in measuring the amount of a binder constituent dispersed through a fibrous mat such as glass wool insulation.

Energy which is radiated through the fibrous mat may be expressed as the exponential function:

$$I = I_O e^{-at} = I_O e^{-\mu \rho t} = I_O e^{-t/T} \quad (1)$$

for a homogeneous material and where a is the attenuation constant equal to $\mu\rho$ and where $\mu$ is the absorption cross section of the material expressed as ft$^2$/lb., $\rho$ is material density expressed as lb/ft$^3$, t is the thickness of the material in the direction of radiation, $I_O$ is the radiated energy intensity seen by the detector 15 when no sample is between the source 13 and the detector 15 and I is the measured intensity of radiation after going through the sample of thickness t.

For a fibrous mat, equation (1) may be further refined as an additional function of thickness (t), fiber diameter (d) fiber orientation (o) frequency (f) of the source and material distribution within the source to sensor path (B) as follows:

$$I = I_O e^{-\mu \rho t} \cdot F(t,d,o,f,B) \quad (2)$$

where the absorption cross section $\mu$ is a function of frequency (f) and material (m).

The value of $\mu$, the absorption cross section can be determined empirically for any material m readiated at any frequency f by measuring the radiated energy $I_o$ and the energy transmitted through the material and where the density $\rho m$ of the material is known.

Solving equation 2 for the absorption cross section umf of material m at frequency f $$\mu_{mf} = \frac{\ln(F(t,d,o,f,B)I_o/I)}{\rho m^t} \quad (3)$$

A sufficiently large number of samples may be chosen so random changes in t, d, o, f and B calcel each other where a single source of energy is used or $\mu_{mf}$ may be determined with reference to the prior art technique of utilizing two closely aligned frequency energy sources f=1 and f=2 to radiate the material. Since the absorption cross section $\mu_{mf}$ is a function of the frequency of the source and of the material, it must be separately determined for each material and for frequencies or wavelengths of interest.

In the case of measuring the amount of first material, which may be constituent material of a binder, dispersed through a second material, which may be a glass fibrous mat, and the case of measuring the amount of a constituent material to determine the process or material state where the first material may be a solid dispersed within the binder or may be the binder liquid carrier, typically a set of five energy frequencies would be used. It should be understood that this set of five frequencies represents an example appropriate where two separate first materials are being measured. In this case a particular first material affects transmission at frequency f=1 and the other particular first material affects transmission at frequency f=2. The number of frequencies of interest is that which can possibly be made smaller or enlarged according to the discussion below.

Where this set of five energy sources at five respective frequencies are employed, the amounts of each of the two separate first materials may be measured at the same time. Using five frequencies it is possible to measure the property of a particular first material, an amine (aliphatic functional group CH$_2$), for example, which does not change in amount during the process cycle and which is indicative of the amount of the amine applied to the fibrous mat or the amount of the amine contained in the binder solution. A first frequency f=1 would be chosen for its sensitivity to the presence of the amine and may be 3.41 microns wavelength. A second closely aligned frequency f=2 is chosen for use as a reference with f=1. A third frequency, f=3, and its reference f=4 is chosen for its sensitivity to the amount of another particular first material, such as water as represented by the hydroxyl functional group, OH. The frequency f=3 has a 3.0 microns wavelength. The measured property of the constituent is indicative of the process or material state.

It should be recognized that the term "first material" is used broadly for any of the materials dispersed in the second material and can mean one or more particular materials within the specified group of first materials.

The set of five frequencies is described as follows:

Frequency f=1 is sensitive to the amount of a first material, binder constituent such as a polymer, dispersed through the second material, and which does not change over the process cycle.

Frequency f=2 is a frequency chosen to be relatively close to f=1 according to the measurement technique used.

Frequency f=2 is chosen for its sensitivity to a first material binder constituent that changes state during the process over time or during a cure cycle and is an indication of process or material state such as cure.

Frequency f=4 is chosen to be relatively close to f=3 according to the measurement technique used.

Frequency f=5 is chosen to be responsive to the presence of the second material and substantially insensitive to the presence of the first material. Frequency f=5 may be in x-ray or gamma-ray in the range of 20 kev and is used to obtain an independent measurement of the weight per area of radiation of the second material.

The invention may be practiced by radiating with a set of energies at three frequencies f=1, f=2 and f=5, for example, to measure the presence of a particular binder constituent dispersed throughout a second material, such as a mat of fibrous glass. Alternatively, the invention might utilize frequency set f=3, f=4 and f=5 where, for example, it is desired to obtain an indication of the cure rate. The energy transmitted through the materials at frequency f=3 would be sensitive to the amount as indicative of the state of the particular first material. In utilizing only a set of three frequencies, the frequency f=1 is chosen to measure the amount of a first material and is insensitive to any of the other first materials dispersed through the second material. Similarly, where a frequency f=3 is chosen to measure change in state, it is insensitive to the amount of other first materials dispersed through the second material.

The number of first materials measured is controlled by the spread between the chosen frequencies responsive to each of the respective first materials and the practical consideration of interference between the separate energy sources at the separate frequencies. It should be recognized that the number of frequencies used may be expanded corresponding to the number of different particular first materials within the general group of first materials to be measured and recognizing the need for the additional energy source responsive to the second material.

For the purpose of the following discussion and to fully illustrate the invention, the practice of using a set of five frequencies will be discussed. However, it should be recognized that this set could be expanded or reduced. In this case, $I_{01}$, $I_{02}$, $I_{03}$, $I_{04}$, and $I_{05}$ are the intensity of the radiated energy as measured by the detector without a sample in place at each of the respective frequencies $f=1$ through $f=5$, and measured radiations after being transmitted through the material at distance t from the source are $I_1$, $I_2$, $I_3$, $I_4$, and $I_5$.

In accordance with the discussion above, the absorption cross section $\mu_{mf}$ of each material or component is measured and known. The general equation for each of the energies transmitted through the material and measured then is $$I_i = I_{0i}p - (\mu_{bi}\rho_b + \mu_{gi}\rho_g + \mu_{ci}\rho_c)t \cdot F(t,d,o,f=i,B) \quad (4)$$

These and the following equations are first order approximations for the purpose of explaining the principles of the invention. One skilled in the art will recognize that there may be a need to add correction terms, as appropriate, to compensate for higher order effects due to reflections and variations in the measurement apparatus and measurement environment.

For the following formulas, $\mu_{bi}$ is the absorption cross section for a particular first material which may be moisture or a phenolic, or any other binder constituent, at frequency $f=1$; $\rho_b$ is the density of a particular first material, $\mu_{gi}$ is the absorption cross section of the fibrous second material, which may be glass, at frequency $f=1$, and $\rho_g$ is the density of the fibrous material, $\mu_{ci}$ is the absorption cross section of another distinct particular first material at frequency $f=1$; and $\rho_c$ is the density of a separate and distinct particular first material; and t is the thickness of the material of the sample.

The full set of five energy sources at five separate frequencies, provides five equations in 8 unknowns as follows:

$$I_1 = I_{01}F(f=1)e - (\mu_{b1}\rho_b + \mu_{g1}\rho_g + \mu_{c1}\rho_c)t \quad (5a)$$

$$I_2 = I_{02}F(f=2)e - (\mu_{b2}\rho_b + \mu_{g2}\rho_g + \mu_{c2}\rho_c)t \quad (5b)$$

$$I_3 = I_{03}F(f=3)e - (\mu_{b3}\rho_b + \mu_{g3}\rho_g + \mu_{c3}\rho_c)t \quad (5c)$$

$$I_4 = I_{04}F(f=4)e - (\mu_{b4}\rho_b + \mu_{g4}\rho_g + \mu_{c4}\rho_c)t \quad (5d)$$

$$I_5 = I_{05}F(f=5)e - (\mu_{b5}\rho_b + \mu_{g5}\rho_g + \mu_{c5}\rho_c)t \quad (5e)$$

The above set of five equations with eight unknowns $[\rho_b, \rho_g, \rho_c, F(f=1), F(f=2), F(f=3), F(F=4), F(f=5)]$ provides an indication for two separate and distinct first materials dispersed within the second material. The five equations are reduced to n equations with n unknowns for solving, for example, they are reduced to three equations with the three unknowns $\rho_b$, $\rho_g$ and $\rho_c$. Solving the equations can provide the amount of a particular first material $\rho_b$ responsive to frequency $f=1$ and a different particular first material $\rho_c$ responsive to frequency $f=3$. Frequency $f=1$ with reference frequency $f=2$ may be responsive to the amount of a binder constituent dispersed through the second material such as the liquid or a solid dispersed in the binder and frequency $f=3$ used with reference frequency $f=4$ may be responsive to the amount of a binder material such as a phenolic dispersed within the second material and may be an indication of process or material state such as binder cure.

Where the energy at frequency $f=5$ is x-ray or gamma-ray, scattering is minimized and $F(f=5)$ is approximately equal to 1 as long as the drop of intensity with distance is normalized by the measurement of $I_{05}$ with the same sensor geometry without any sample in place. The particular energy source for frequency $f=5$ should be capable of being transmitted through the material at thickness t, and any suitable signal source may be used.

Accordingly, the scattering $[F(t,d,O,f,B)]$ should be similar for the closely aligned frequencies $f=1$ and $f=2$, and for $f=3$ and $f=4$ so that $F(f=1)$ approximately equals $F(f=2)$ and $F(f=3)$ approximately equals $F(f=4)$.

Equation 5a and 5b and equations 5c and 5d corresponding to the measured intensities for the two sets of closely aligned frequencies, and equation 5c may then be rearranged as follows by dividing equation 5a by 5b and equation 5c by 5d:

$$\frac{I}{t}\ln\left(\frac{(I_2 I_{01})}{(I_{02} I_1)}\right) = \rho_b(\mu_{b1} - \mu_{b2}) + \rho_g(\mu_{g1} - \mu_{g2}) + \rho_c(\mu_{c1} - \mu_{c2}) \quad (6a)$$

$$\frac{I}{t}\ln\left(\frac{(I_4 I_{03})}{(I_{04} I_3)}\right) = \rho_b(\mu_{b3} - \mu_{b4}) + \rho_g(\mu_{g3} - \mu_{g4}) + \rho_c(\mu_{c3} - \mu_{c4}) \quad (6b)$$

$$\frac{I}{t}\ln\left(\frac{(I_{05}(F=1)}{(I_5)}\right) = \rho_b(\mu_{b5}) + \rho_g(\mu_{g5}) + \rho_c(\mu_{c5}) \quad (6c)$$

These equations provide an indication of the second material density which is used in determining either $\rho_b$ or $\rho_c$ and which can be used to analyze the effect of the second material on the measurement of the first materials by simultaneous solution of the set of three equations 6a, 6b and 6c.

Given the known source intensity ($I_{01}$ through $I_{05}$), the measured energy intensity ($I_1$ through $I_5$) after passing through the materials, the absorption cross sections for each of the materials at each of the responsive frequencies ($\mu_{b1} - \mu_{b5}$; $\mu_{g1} - \mu_{g5}$; and $\mu_{c1} - \mu_{c5}$), and the thickness t of the material, then the set of three equations can be solved using standard methods such as determinates except where the determinates equal zero. A digital computer, shown at 16 in FIG. 2, can be programmed to process the measured signals corresponding to $I_{01} - I_{05}$ and $I_1 - I_5$ according to the relationships of equation 6a-6c to determine the unknown densities $\rho_b$, $\rho_g$, and $\rho_c$.

It should be recognized that a plurality of separate first materials may be measured. Where n first materials were dispersed in a second material then n frequencies would be chosen. Each of the n frequencies is selected to be responsive to a separate particular first material and each of the n frequencies having an appropriate reference frequency. Consistent with the measurement technique, a total of n+1 responsive frequencies and up to n+1 reference frequencies will be used with the $n^{th}+1$ frequency being responsive to the second material.

Where it is desired to identify the amount or density of only one particular first material of several first materials dispersed through the second material this method may be used. A set of three frequencies are selected, such as frequencies f=1, f=2 and f=5 or frequencies f=3, f=4 and f=5, depending upon which particular first material is to be measured and provided the unmeasured material does not affect the selected frequencies significantly.

If it is desired to measure the amount of a binder constituent material dispersed within the fibrous material then two closely related frequencies are chosen corresponding to a particular first material whose amount is constant over the process cycle. The first frequency f=1 is selected to be responsive to the presence of that first material and the second frequency f=2 is a closely aligned frequency which is relatively insensitive to the presence of that the first material and provide a reference. In this case, the energy at frequency f=1 is substantially insensitive to any other particular first material which is separate and distinct from the particular first material measured. The fifth frequency f=5 in this case is selected to be sensitive to the presence of the second material and relatively insensitive to the presence of the first material. As discussed above, it would be necessary to experimentally obtain the absorption cross section u for the first and the second materials at each of the three frequencies being used. This is necessary in order to find the absorption cross section for each of the materials of each of the frequencies being used. Since only one first material is measured, the equations 6a, 6b and 6c will be reduced to two equations with two unknowns. The terms containing the other unknown, $\rho_b$ or $\rho_c$, will drop out of the equations.

In summary, this invention is directed to a method and apparatus for determining the amount or state of a first material dispersed within a second material. The term "first material" used herein is used generally to denote one or more particular first materials dispersed within the second material and a separate responsive frequency is used for each particular first material of the group of first materials to be measured. It should be appreciated that various changes and modifications may be made in the above described embodiments of the invention without departing from the spirit and the scope of the following claims.

We claim:

1. A method for measuring binder characteristics in a mat of binder-coated glass fibers, said binder having a cure indicator constituent, the amount of which changes as said binder is cured, comprising radiating said mat and said binder with first, second and third energies, said first energy having a wavelength which is absorbed by said binder, but is substantially not absorbed by said cure indicator constituent, said second energy having a wavelength which is absorbed by said binder including said cure indicator constituent, and said third energy having a wavelength which is substantially not absorbed by either said binder or said cure indicator constituent;

sensing the amount of said first, second and third energies transmitted through said mat; and, determining the amount of binder contained in said mat from the sensed energies.

2. The method of claim 1 in which said binder comprises a phenolic resin in which an amine absorbs said first energy.

3. The method of claim 1 comprising the further step of determining the amount of said cure indicator constituent in said binder from the sensed energies.

4. The method of claim 3 comprising determining the degree of cure of said binder from the amount of said cure indicator constituent.

5. The method of claims 3 or 4 in which said binder comprises a phenolic resin, and said cure indicator constituent comprises the hydroxyl functional group, OH.

6. The method of claims 1 or 3 in which each determining step comprises solving first and second equations for $\rho_1$ where said first equation is defined as $$(1/t)\ln[(I_2 I_{01})/(I_{02} I_1)] = \rho_1(\mu_{11}-\mu_{12}) + \rho_2(\mu_{21}-\mu_{22})$$

and said second equation is defined as $$(1/t)\ln(I_{03}/I_3) = \rho_1\mu_{13} - \rho_2\mu_{23}$$

where $I_{01}$: intensity of said first energy;
$I_{02}$: intensity of said second energy;
$I_{03}$: intensity of said third energy;
$I_1$: sensed intensity of said first energy;
$I_2$: sensed intensity of said second energy;
$I_3$: sensed intensity of said third energy; p1 t: thickness of said mat;
$\rho_1$: density of said binder;
$\rho_2$: density of said glass fibers;
$\mu_{11}$: absorption cross-section of the binder and cure indicator constituent for said first energy;
$\mu_{12}$: absorption cross-section of the binder and cure indicator constituent for said second energy;
$\mu_{13}$: absorption cross-section of the binder and cure indicator constituent for said third energy;
$\mu_{21}$: absorption cross-section of said glass fibers for said first energy;
$\mu_{22}$: absorption cross-section of said glass fibers for said second energy; and
$\mu_{23}$: absorption cross-section of said glass fibers for said third energy.

7. The method of claim 6 comprising solving said first and second equations for $\rho_2$ to determine the density of the glass fibers.

* * * * *